United States Patent
Peiffer et al.

(10) Patent No.: US 9,610,533 B2
(45) Date of Patent: Apr. 4, 2017

(54) ORGANO-AMINE ACID GAS ADSORPTION-DESORPTION POLYMERS, PROCESSES FOR PREPARING SAME, AND USES THEREOF

(71) Applicants: Dennis G. Peiffer, Annandale, NJ (US); David C. Calabro, Bridgewater, NJ (US); Quanchang Li, Dayton, NJ (US); Mobae Afeworki, Phillipsburg, NJ (US); Stephen M. Cundy, Lebanon, NJ (US)

(72) Inventors: Dennis G. Peiffer, Annandale, NJ (US); David C. Calabro, Bridgewater, NJ (US); Quanchang Li, Dayton, NJ (US); Mobae Afeworki, Phillipsburg, NJ (US); Stephen M. Cundy, Lebanon, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 17 days.

(21) Appl. No.: 14/791,772

(22) Filed: Jul. 6, 2015

(65) Prior Publication Data
US 2015/0307661 A1    Oct. 29, 2015

Related U.S. Application Data

(62) Division of application No. 13/332,500, filed on Dec. 21, 2011, now Pat. No. 9,115,260.
(Continued)

(51) Int. Cl.
C07C 211/13    (2006.01)
C07C 211/14    (2006.01)
(Continued)

(52) U.S. Cl.
CPC ............ B01D 53/02 (2013.01); B01D 53/40 (2013.01); B01D 53/62 (2013.01); B01J 20/262 (2013.01);
(Continued)

(58) Field of Classification Search
None
See application file for complete search history.

(56) References Cited

U.S. PATENT DOCUMENTS 3,134,740 A * 5/1964 Sheetz .................... B01J 45/00
                                                    106/1.27
8,557,027 B2    10/2013 Peiffer et al.
(Continued)

FOREIGN PATENT DOCUMENTS

WO    2010091831 A1    8/2010

OTHER PUBLICATIONS

Sartori et al., "Sterically Hindered Amines for CO2 Removal from Gases", Industrial & Engineering Chemistry Fundamentals, May 1, 1983, 239-249, vol. 22, iss. 2, ACS Publications.
(Continued)

Primary Examiner — Daniel Berns
(74) Attorney, Agent, or Firm — Andrew T. Ward

(57) ABSTRACT

An adsorption-desorption material, in particular, crosslinked organo-amine polymeric materials having a weight average molecular weight of from about 500 to about $1 \times 10^6$, a total pore volume of from about 0.2 cubic centimeters per gram (cc/g) to about 2.0 cc/g, and an adsorption capacity of at least about 0.2 millimoles of $CO_2$ adsorbed per gram of adsorption-desorption material, and linear organo-amine polymeric materials having a weight average molecular weight of from about 160 to about $1 \times 10^6$, a total pore volume of from about 0.2 cubic centimeters per gram (cc/g) to about 2.0 cc/g, and an adsorption capacity of at least about
(Continued)

0.2 millimoles of $CO_2$ adsorbed per gram of adsorption-desorption material. This disclosure also relates in part to processes for preparing the crosslinked organo-amine materials and linear organo-amine materials. This disclosure further relates in part to the selective removal of $CO_2$ and/or other acid gases from a gaseous stream containing one or more of these gases using the adsorption-desorption materials.

10 Claims, 2 Drawing Sheets

Related U.S. Application Data

(60) Provisional application No. 61/426,183, filed on Dec. 22, 2010.

(51) Int. Cl.

| | | |
|---|---|---|
| *C08J 9/00* | (2006.01) | |
| *B01J 20/26* | (2006.01) | |
| *B01J 20/28* | (2006.01) | |
| *B01J 20/30* | (2006.01) | |
| *C08G 73/00* | (2006.01) | |
| *C08G 73/02* | (2006.01) | |
| *B01D 53/02* | (2006.01) | |
| *B01D 53/62* | (2006.01) | |
| *C08J 9/26* | (2006.01) | |
| *C08J 9/28* | (2006.01) | |
| *B01J 20/34* | (2006.01) | |
| *B01D 53/40* | (2006.01) | |
| *C07C 211/53* | (2006.01) | |
| *C08J 9/14* | (2006.01) | |

(52) U.S. Cl.
CPC ........... *B01J 20/264* (2013.01); *B01J 20/267* (2013.01); *B01J 20/28057* (2013.01); *B01J 20/28069* (2013.01); *B01J 20/28078* (2013.01); *B01J 20/3085* (2013.01); *B01J 20/3425* (2013.01); *B01J 20/3483* (2013.01); *B01J 20/3491* (2013.01); *C07C 211/53* (2013.01); *C08G 73/00* (2013.01); *C08G 73/02* (2013.01); *C08G 73/0206* (2013.01); *C08J 9/141* (2013.01); *C08J 9/26* (2013.01); *C08J 9/28* (2013.01); *B01D 2251/80* (2013.01); *B01D 2253/202* (2013.01); *B01D 2253/311* (2013.01); *B01D 2256/24* (2013.01); *B01D 2257/504* (2013.01); *B01D 2258/0283* (2013.01); *B01J 2220/56* (2013.01); *C08J 2201/026* (2013.01); *C08J 2201/0502* (2013.01); *C08J 2203/14* (2013.01); *C08J 2379/02* (2013.01); *Y02C 10/04* (2013.01); *Y02C 10/08* (2013.01); *Y02P 20/152* (2015.11); *Y10T 428/2982* (2015.01)

(56) References Cited

U.S. PATENT DOCUMENTS

| | | |
|---|---|---|
| 2007/0149398 A1 | 6/2007 | Jones et al. |
| 2011/0226697 A1 | 9/2011 | McLellan et al. |
| 2012/0164044 A1 | 6/2012 | Peiffer et al. |
| 2012/0164045 A1 | 6/2012 | Peiffer et al. |

OTHER PUBLICATIONS

Hagg et al., "CO2 Capture from Natural Gas Fired Power Plants by Using Membrane Technology" Industrial & Engineering Chemistry Research, Jul. 8, 2005, pp. 7668-7675, vol. 44, iss. 20, ACS Publications.
Alauzun et al.,"CO2 as a Supramolecular Assembly Agent: A Route for Lamellar Materials with a High Content of Amine Groups", Journal of the American Chemical Society, Jul. 23, 2005, pp. 11204-11205, vol. 127, No. 32, ACS Publications.
Gray et al., "Improved immobilized carbon dioxide capture sorbents", Fuel Processing Technology, Oct. 2005, pp. 1449-1455, vol. 86, iss. 14-15, Elsevier, ScienceDirect.
Harlick et al., "Applications of Pore-Expanded Mesoporous Silicas. 3. Triamine Silane Grafting for Enhanced CO2 Adsorption", Industrial & Engineering Chemistry Research, Mar. 22, 2006, pp. 3248-3255, vol. 45, iss. 9, ACS Publications.
Yue et al., "CO2 Capture by As-Prepared SBA-15 with an Occluded Organic Template", Advanced Functional Materials, Jul. 25, 2006, pp. 1717-1722, vol. 16, iss. 13, Wiley-VCH Verlag GmbH & Co. KGaA, Weinheim.
Zou et al., "CO2-selective polymeric membranes containing amines in crosslinked poly(vinyl alcohol)", Journal of Membrane Science, Oct. 10, 2006, pp. 310-321, vol. 286, Science Direct, Elsevier.
Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458, vol. 46, iss. 2, ACS Publications.
Jadhav et al., "Monoethanol Amine Modified Zeolite 13X for CO2 Adsorption at Different Temperatures", Energy & Fuels, Sep. 28, 2007, pp. 3555-3559, vol. 21, iss. 6, ACS Publications.
Li et al., "Preparation and Adsorption Properties of Polyethylenimine Containing Fibrous Adsorbent for Carbon Dioxide Capture", Journal of Applied Polymer Science, Mar. 12, 2008, pp. 3851-3858, vol. 108, iss. 6, Wiley Periodicals, Inc.
Office Action from related U.S. Appl. No. 13/332,500 dated May 19, 2015.

\* cited by examiner

| Sorbent | Tads/Tdes (1) | mmoles CO2/g | mmoles CO2/mmole N | cycle stable? |
|---|---|---|---|---|
| Polyethylenamine/SiO2 | 35°C/85°C | 0.23/2.44) | 0.24 | |
| AP-SBA | 25°C/130°C | 0.4 | 0.21 | yes |
| Diamine-SBA | 25°C/130°C | 0.7 | 0.28 | yes |
| Polyethylenamine/SBA (olig.) | 85°C/85°C | 0.5 (1.61) | | |
| Polyethylenamine/SBA (750k) | 25°C/130°C | 2.0 | 0.27 | no |
| TEPA/SBA | 25°C/130°C | 2.74 | 0.26 | no |
| GT-HAS | 25°C/130°C | 3.11* | 0.44 | |
| DCX-Polyethylenamine 423 | 85°C | 4.1 | 0.29 | yes |
| Pure Polyethylenamine | 35°C/85°C | 0.77 | 0.29 | |

*2.0 mmoles CO2/g @ 75°C, (1) Tads/Tdes adsorption temperature / desorption temperature

ORGANO-AMINE ACID GAS ADSORPTION-DESORPTION POLYMERS, PROCESSES FOR PREPARING SAME, AND USES THEREOF

This application is a divisional application of U.S. application Ser. No. 13/332,500, which claims the benefit of U.S. Provisional Application No. 61/426,183 filed Dec. 22, 2010.

BACKGROUND

Field of the Disclosure

This disclosure relates in part to adsorption-desorption materials, in particular, to crosslinked organo-amine materials, and linear organo-amine materials, and to processes for the preparation of these materials. This disclosure also relates in part to the use of these materials in the selective removal of $CO_2$ and/or other acid gases from a gaseous stream containing one or more of these gases.

Discussion of the Background Art

The selective removal of carbon dioxide from mixed gas streams is of great commercial value. Commercially, carbon dioxide may be used for reinjection into gas or liquid hydrocarbon deposits to maintain reservoir pressure and for enhanced product recovery. Due to the advanced age of many producing reservoirs worldwide and the ever-increasing challenge of meeting demand, the expanding use of enhanced oil recovery (EOR) methods is becoming more widespread.

Typically the source of carbon dioxide for EOR is the producing hydrocarbon stream itself, which may contain anywhere from less than 5% to more than 80% of $CO_2$.

Additionally, it is desired to capture $CO_2$ from flue gas of various combustion sources, where the stream contains less than about 15% of $CO_2$ and its temperature is relatively high. Yet another need for $CO_2$ capture technology is for the pre-combustion capture of $CO_2$ from shifted syngas produced in fuel gasification processes.

Conventional methods for $CO_2$ capture include cryogenic distillation/condensation, absorption using liquid solvents, such as amine scrubbing, or sorption using solid sorbents, such as pressure swing adsorption (PSA) and/or temperature swing adsorption (TSA). However, with present technologies, all of these processes require a large temperature decrease of the gas stream to enable $CO_2$ condensation or sorption. Conventional methods (PSA, TSA, amine scrubbing) require $CO_2$ uptake at relatively low temperatures (e.g., less than 50° C.). Sorbent/solvent regeneration ($CO_2$ desorption) is accomplished by a step change decrease in $CO_2$ partial pressure (PSA), and/or by a temperature increase to above about 100° C. (TSA, amine scrubbing). In all of these cases, $CO_2$ capture costs depend significantly on the required heat exchange capacities and energy requirements for gas cooling/heating, the costs for steam generation for $CO_2$ desorption, and the high equipment and energy costs associated with $CO_2$ recompression.

Conventional amine scrubbing is based on the chemistry of $CO_2$ with amines to generate carbonate/bicarbonate and carbamate salts. Commercially, amine scrubbing typically involves contacting the $CO_2$ and/or $H_2S$ containing gas stream with an aqueous solution of one or more simple amines (e.g., monoethanolamine). The process requires high rates of gas-liquid exchange and the transfer of large liquid inventories between the absorption and regeneration steps and high energy requirements for the regeneration of amine solutions. This process is challenged by the corrosive nature of the amine solutions. These challenges limit the economic viability for large-scale applications (e.g., large combustion sources and power plants) utilizing conventional technologies.

The growing need to incorporate carbon capture and sequestration (CCS) into fossil fuel-based power generation, has triggered accelerating research into alternatives to conventional amine scrubbing technology. Cyclic adsorption technologies (e.g., PSA and TSA) using solid adsorbents are also well-known in the gas purification industry. These processes avoid many of the limitations of amine scrubbing described above, but suffer from a lack of adsorbents having sufficiently selective $CO_2$ adsorption under the humid conditions always present in combustion flue gas, as well as the commercial viability of large scale operation.

Due to the ever increasing use of $CO_2$ re-injection for enhanced oil recovery, technology that reduces the cost of $CO_2$ capture directly reduces hydrocarbon production costs. In addition, if anticipated future restrictions on $CO_2$ emissions are mandated, a low cost method for $CO_2$ capture will be a critical need as a part of CCS.

Carbon dioxide is a ubiquitous and inescapable by-product of the combustion of hydrocarbons. In addition to the use of $CO_2$ for EOR, there is growing concern over its accumulation in the atmosphere and its role in global climate change. Therefore in addition to the commercial benefits of $CO_2$ recovery, environmental factors may soon require its capture and sequestration. For these reasons the separation of $CO_2$ from mixed gas streams is a rapidly growing area of research.

Therefore, a need exists for developing commercially viable alternative methods and adsorbent materials for the selective removal of $CO_2$ from gas mixtures, particularly adsorption technologies and adsorbent materials having economic viability for large-scale (e.g., large combustion sources and power plants) applications.

SUMMARY OF THE DISCLOSURE

This disclosure relates in part to an acid gas adsorption-desorption material comprising a crosslinked organo-amine material having a weight average molecular weight of from about 500 to about $1\times10^6$, a total pore volume of from about 0.2 cubic centimeters per gram (cc/g) to about 2.0 cc/g, and an adsorption capacity of at least about 0.2 millimoles of $CO_2$ adsorbed per gram of adsorption-desorption material, or mixtures thereof.

This disclosure also relates in part to an acid gas adsorption-desorption material comprising a linear organo-amine material having a weight average molecular weight of from about 160 to about $1\times10^6$, a total pore volume of from about 0.2 cubic centimeters per gram (cc/g) to about 2.0 cc/g, and an adsorption capacity of at least about 0.2 millimoles of $CO_2$ adsorbed per gram of adsorption-desorption material, or mixtures thereof.

This disclosure further relates in part to a process for preparing an acid gas adsorption-desorption material comprising a crosslinked organo-amine material having a weight average molecular weight of from about 500 to about $1\times10^6$, a total pore volume of from about 0.2 cubic centimeters per gram (cc/g) to about 2.0 cc/g, and an adsorption capacity of at least about 0.2 millimoles of $CO_2$ adsorbed per gram of adsorption-desorption material, or mixtures thereof; said process comprising (i) reacting at least one organo halide material comprised of at least two haloalkyl functional groups, with at least one organo-amine material under conditions sufficient to produce an organo-amine material, and (ii) crosslinking said organo-amine material under conditions sufficient to produce said crosslinked organo-amine material.

This disclosure yet further relates in part to a process for preparing an acid gas adsorption-desorption material comprising a linear organo-amine material having a weight average molecular weight of from about 160 to about $1 \times 10^6$, a total pore volume of from about 0.2 cubic centimeters per gram (cc/g) to about 2.0 cc/g, and an adsorption capacity of at least about 0.2 millimoles of $CO_2$ adsorbed per gram of adsorption-desorption material, or mixtures thereof; the process comprising reacting at least one organo halide material comprised of at least two haloalkyl functional groups, with at least one organo-amine material under conditions sufficient to produce said linear organo-amine material.

This disclosure also relates in part to a method for adsorption-desorption of an acid gas comprising:

contacting a gas mixture containing at least one acid gas with an adsorbent material under conditions sufficient to cause adsorption of at least a portion of the acid gas, the adsorbent material comprising a crosslinked organo-amine material having a weight average molecular weight of from about 500 to about $1 \times 10^6$, a total pore volume of from about 0.2 cubic centimeters per gram (cc/g) to about 2.0 cc/g, and an adsorption capacity of at least about 0.2 millimoles of $CO_2$ adsorbed per gram of adsorbent material, or mixtures thereof; and treating the adsorbent material under conditions sufficient to cause desorption of at least a portion of the acid gas.

This disclosure further relates in part to a method for adsorption-desorption of an acid gas comprising:

contacting a gas mixture containing at least one acid gas with an adsorbent material under conditions sufficient to cause adsorption of at least a portion of the acid gas, the adsorbent material comprising a linear organo-amine material having a weight average molecular weight of from about 160 to about $1 \times 10^6$, a total pore volume of from about 0.2 cubic centimeters per gram (cc/g) to about 2.0 cc/g, and an adsorption capacity of at least about 0.2 millimoles of $CO_2$ adsorbed per gram of adsorbent material, or mixtures thereof; and treating the adsorbent material under conditions sufficient to cause desorption of at least a portion of the acid gas.

This disclosure yet further relates in part to a method for adsorption-desorption of carbon dioxide comprising:

contacting a gas mixture containing at least carbon dioxide with an adsorbent material under conditions sufficient to cause adsorption of at least a portion of the carbon dioxide, the adsorbent material comprising a crosslinked organo-amine material having a weight average molecular weight of from about 500 to about $1 \times 10^6$, a total pore volume of from about 0.2 cubic centimeters per gram (cc/g) to about 2.0 cc/g, and an adsorption capacity of at least about 0.2 millimoles of $CO_2$ adsorbed per gram of adsorbent material, or mixtures thereof; and treating the adsorbent material under conditions sufficient to cause desorption of at least a portion of the carbon dioxide.

This disclosure also relates in part to a method for adsorption-desorption of carbon dioxide comprising:

contacting a gas mixture containing at least carbon dioxide with an adsorbent material under conditions sufficient to cause adsorption of at least a portion of the carbon dioxide, the adsorbent material comprising a linear organo-amine material having a weight average molecular weight of from about 160 to about $1 \times 10^6$, a total pore volume of from about 0.2 cubic centimeters per gram (cc/g) to about 2.0 cc/g, and an adsorption capacity of at least about 0.2 millimoles of $CO_2$ adsorbed per gram of adsorbent material, or mixtures thereof; and treating the adsorbent material under conditions sufficient to cause desorption of at least a portion of the carbon dioxide.

This disclosure further relates in part to a method of separating carbon dioxide from a gas mixture comprising:

providing at least one adsorption zone comprising an adsorbent, the adsorbent comprising a crosslinked organo-amine material having a weight average molecular weight of from about 500 to about $1 \times 10^6$, a total pore volume of from about 0.2 cubic centimeters per gram (cc/g) to about 2.0 cc/g, and an adsorption capacity of at least about 0.2 millimoles of $CO_2$ adsorbed per gram of adsorbent material, or mixtures thereof;

passing the gas mixture comprising at least carbon dioxide through the at least one adsorption zone, wherein the adsorbent adsorbs at least part of the carbon dioxide from the mixture to provide a carbon dioxide-depleted gas; and regenerating the adsorbent to provide a carbon dioxide-rich gas.

This disclosure yet further relates in part to a method of separating carbon dioxide from a gas mixture comprising:

providing at least one adsorption zone comprising an adsorbent, the adsorbent comprising a linear organo-amine material having a weight average molecular weight of from about 160 to about $1 \times 10^6$, a total pore volume of from about 0.2 cubic centimeters per gram (cc/g) to about 2.0 cc/g, and an adsorption capacity of at least about 0.2 millimoles of $CO_2$ adsorbed per gram of adsorbent material, or mixtures thereof;

passing the gas mixture comprising at least carbon dioxide through the at least one adsorption zone, wherein the adsorbent adsorbs at least part of the carbon dioxide from the mixture to provide a carbon dioxide-depleted gas; and regenerating the adsorbent to provide a carbon dioxide-rich gas.

The adsorbent materials useful in this disclosure have the advantage of recovery of $CO_2$ at low pressure, low capital costs, low propensity for corrosion, and low regeneration energy compared to conventional processes where a large amount of energy is required to heat the aqueous amine solution.

The adsorbent material useful in this disclosure possesses high $CO_2$ uptake capacity at temperatures from about 20° C. to about 160° C. This is significantly higher temperatures than where most conventional sorbents can operate. At these higher temperatures, where conventional sorbents (e.g., liquid amines, zeolites, and carbons) usually undergo $CO_2$ desorption, the adsorbent material of this disclosure exhibits substantial and quite rapid $CO_2$ uptake. Complete $CO_2$ desorption can be accomplished by a partial pressure swing, wherein the $CO_2$-containing feed gas is replaced in the desorption step with an essentially $CO_2$-free or low $CO_2$ content purge gas or fluid under essentially isothermal conditions. Using this $CO_2$ sorbent material, the need for temperature cycling is minimized and a rapid cycle partial pressure swing adsorption can be carried out at much higher temperature, as well as essentially isothermal conditions than practiced with conventional sorbents, thereby greatly reducing the heat exchange cost of $CO_2$ separation.

As used herein, "essentially isothermal conditions" means at or about the same temperature. In a preferred embodiment, the adsorption-desorption processes of this disclosure are carried out under essentially isothermal conditions.

Further objects, features and advantages of the present disclosure will be understood by reference to the following drawings and detailed description.

BRIEF DESCRIPTION OF THE FIGURES

FIG. 3 shows $CO_2$ uptake capacity data from a variety of polyethyleneimines and aminosilane-modified materials.

DETAILED DESCRIPTION OF THE PREFERRED EMBODIMENT

Figure 1:
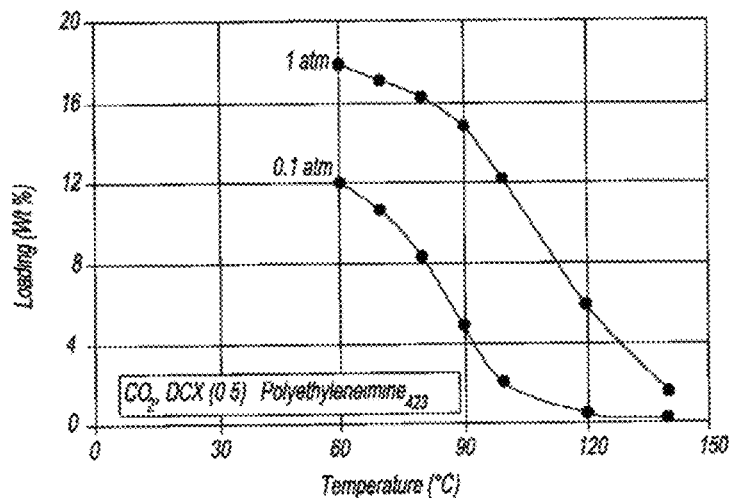
FIG. 1 graphically depicts gravimetric uptake of the adsorbent prepared in Example 2.

The acid gas adsorption-desorption materials of this disclosure comprise in part crosslinked organo-amine polymeric materials. The crosslinked organo-amine materials have a weight average molecular weight of from about 500 to about $1 \times 10^6$, preferably a weight average molecular weight of from about 600 to about $1 \times 10^5$, and more preferably a weight average molecular weight of from about $1 \times 10^3$ to about $5 \times 10^4$. The crosslinked organo-amine materials have an adsorption capacity of at least about 0.2 millimoles of $CO_2$ adsorbed per gram of adsorption-desorption material, preferably an adsorption capacity of at least about 0.5 millimoles of $CO_2$ adsorbed per gram of adsorption-desorption material, and more preferably an adsorption capacity of at least about 1.0 millimoles of $CO_2$ adsorbed per gram of adsorption-desorption material. This disclosure also includes mixtures of the crosslinked organo-amine materials.

Illustrative crosslinked organo-amine materials of this disclosure have a formula selected from:

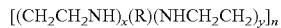

wherein x is an integer greater than about 1.0, y is an integer greater than about 1.0, n is an integer equal to or greater than about 1.0, the $CH_2CH_2NH$ and $NHCH_2CH_2$ groups can be linear or branched, and R is the same or different and is an alkyl or aryl moiety. In a preferred embodiment, at least one R is an aryl moiety. The structure can be terminated with either of the starting monomers as well as monofunctional amines and monofunctional aryl and/or alkyl halides.

The organo halide and organo-amine monomers can both or independently be difunctional and/or multifunctional. In cases where both monomers are difunctional, the product will be a linear organo-amine polymer. If either the organo halide or organo-amine monomers have at least three functional groups, the product will be a crosslinked organo-amine polymer.

As used herein, "crosslinked" means polymer chains that are connected to one another through bonds. Crosslinks are bonds that link one polymer chain to another. When the polymer chains are connected to each other, they lose some of their ability to move as independent polymer chains.

The composition of the crosslinked organo-amine materials of this disclosure, including all polymers, copolymers and terpolymers thereof, can vary over a wide range, and need only be that amount necessary to provide the desired adsorption-desorption properties. These materials can be formed as bulk solids, films, membranes and particulates.

Preferably, the crosslinked organo-amine polymer materials of this disclosure have an average particle diameter of from about 0.1 microns to about 500 microns, preferably from about 1.0 microns to about 100 microns, and more preferably from about 2.0 microns to about 50 microns. Preferably, the crosslinked organo-amine polymer materials of this disclosure have a total pore volume of from about 0.2 cubic centimeters per gram (cc/g) to about 2.0 cc/g, preferably from about 0.4 cc/g to about 2.0 cc/g, and more preferably from about 0.5 cc/g to about 2.0 cc/g, as measured by mercury porsimetry in cubic centimeters of pore volume per gram of the porous crosslinked organo-amine materials, for all pores having a diameter of 0.005 microns to 10 microns.

Preferably, the crosslinked organo-amine polymer materials of this disclosure have an average pore size of from about 0.01 microns to about 1000 microns, preferably from about 0.1 microns to about 100 microns, and more preferably from about 1.0 microns to about 10 microns. Preferably, the crosslinked organo-amine polymer materials of this disclosure have a surface area of from about 5 square meters per gram ($m^2/g$) to about 50 $m^2/g$, preferably from about 20 $m^2/g$ to about 50 $m^2/g$, and more preferably from about 25 $m^2/g$ to about 50 $m^2/g$, as measured by mercury porsimetry.

The crosslinked organo-amine materials of this disclosure can be prepared by a process that involves reacting at least one organo halide material with at least one organo-amine material under conditions sufficient to produce the crosslinked organo-amine material. In particular, the crosslinked organo-amine materials can be produced by reacting at least one organo halide or mixtures of organo halides, with at least one linear amine, branched amine, polyamine, or mixtures thereof, under conditions sufficient to produce the crosslinked organo-amine material.

Illustrative organo halide starting materials useful in making the crosslinked organo-amine materials of this disclosure may be selected from a wide variety of materials known in the art. Illustrative organo halide starting materials include, for example, benzylic halide and mixtures thereof. Preferably, the organo halide is selected from the group consisting of: methylbenzyl chloride, dichloro-p-xylene, crosslinked polystyrene spheres with chemically attached chloromethylstyrene, and mixtures thereof. Halide starting materials which possess at least two haloalkyl functional groups can be prepared by conventional methods known in the art and/or are commercially available.

Illustrative amine starting materials useful in making the crosslinked organo-amine materials of this disclosure may be selected from a wide variety of materials known in the art. Illustrative organo-amine starting materials include, for example, primary amines, secondary amines, and mixtures thereof. Suitable polyamines include, for example, linear polyamines, branched polyamines, polyalkyleneimines, and mixtures thereof. Preferably, the organo-amine is selected from propylenediamine, tetraethylenepentaamine, branched and linear polyethyleneimines, and mixtures thereof. The organo-amine starting materials can be prepared by conventional methods known in the art and/or are commercially available.

As indicated above, mixtures of halide starting materials can be used in making the crosslinked organo-amine materials of this disclosure. For example, one or more aromatic compounds having at least two haloalkyl functional groups may be used in the halide starting material mixtures in the process of this disclosure. These compounds may be used alone or in combination with the alkyl halide compounds described below. Illustrative aromatic compounds having at least two haloalkyl functional groups include, for example, 2,4-bis(chloromethyl)-1,3,5-trimethylbenzene, 2,4,6-tris-(chloromethyl)-mesitylene, 1,3,5-tris-chloromethyl-2,4,6-trimethylbenzene, and mixtures thereof. These aromatic compounds having at least two haloalkyl functional groups can be prepared by conventional methods known in the art and/or are commercially available.

One or more alkyl halides may also be used as starting materials in the process of this disclosure. These compounds may be used either alone or in combination with the aromatic compounds having at least one haloalkyl functional group described above. These compounds may be used alone or in combination with the aromatic compounds having at least two haloalkyl functional groups described above. Illustrative alkyl halides include, for example, polyhalo-alkanes and polyhalo-alkenes having from 1 to about 12 carbon atoms. The polyhalo-alkanes and polyhalo-alkenes can be linear or branched, and contain two or more halide groups with no limit placed on their location on the alkane or alkene chain. The alkene chain can contain one or more carbon-carbon multiple bonds of indeterminate location on the chain. Mixtures of alkyl halides are also useful in this disclosure. These alkyl halide starting materials can be prepared by conventional methods known in the art and/or are commercially available.

Monofunctional reactants can be incorporated as potential structure disruptors and/or pore modifiers for functionality control. A non-limiting example of a monofunctional reactant is methylbenzyl chloride.

A wide variation of crosslinkers can be useful in this disclosure. Crosslinker modifications and network functionality can provide enhanced performance. The crosslinker structure can be varied (tri-/tetra-functional crosslinkers) as well as the crosslink density. Illustrative crosslinkers include, for example, 2,4-bis(chloromethyl)-1,3,5-trimethylbenzene, 2,4,6-tris-(chloromethyl)-mesitylene, 1,3,5-tris-chloromethyl-2,4,6-trimethylbenzene, and mixtures thereof, and the like.

One or more porogens may also be used as a component material in the fabrication processes and crosslinked polymers of this disclosure. An interpenetrating network of holes, closed cells or a combination thereof can be achieved in the crosslinked polymers of this disclosure by polymerization in the presence of an insoluble material such as a porogen. Subsequent removal of the porogen gives rise to interstices throughout the formed crosslinked polymer material. Porogen concentrations in the range of from about 1.0 weight percent to about 75 weight percent, preferably from about 5 weight percent to about 50 weight percent, and more preferably from about 10 weight percent to about 30 weight percent, with respect to the overall reaction mixture, should be sufficient for most processes. Illustrative porogens include, for example, xylene, toluene, polyvinylpyrrolidinone, and mixtures thereof. The porogens can be prepared by conventional methods known in the art and/or are commercially available.

The concentration of the organo halide starting material in the process of this disclosure can vary over a wide range, and need only be that minimum amount necessary to react with the organo-amine starting material and to provide the crosslinked organo-amine materials of this disclosure. In general, depending on the size of the reaction mixture, organo halide starting material concentrations in the range of from about 1.0 weight percent to about 75 weight percent, preferably from about 5 weight percent to about 50 weight percent, and more preferably from about 10 weight percent to about 30 weight percent, with respect to the overall reaction mixture, should be sufficient for most processes.

The concentration of the organo-amine starting material in the process of this disclosure can vary over a wide range, and need only be that minimum amount necessary to react with the organo halide starting material and to provide the crosslinked organo-amine materials of this disclosure. In general, depending on the size of the reaction mixture, organo-amine starting material concentrations in the range of from about 1.0 weight percent to about 75 weight percent, preferably from about 5 weight percent to about 50 weight percent, and more preferably from about 10 weight percent to about 30 weight percent, with respect to the overall reaction mixture, should be sufficient for most processes.

The concentration of the crosslinkers in the process of this disclosure can vary over a wide range, and need only be that minimum amount necessary to achieve desired crosslinking in the crosslinked organo-amine materials of this disclosure. In general, depending on the size of the reaction mixture, concentrations of crosslinkers in the range of from about 0.5 weight percent to about 50 weight percent, preferably from about 1.0 weight percent to about 40 weight percent, and more preferably from about 2.0 weight percent to about 30 weight percent, with respect to the overall reaction mixture, should be sufficient for most processes.

The concentration of the porogens in the process of this disclosure can vary over a wide range, and need only be that minimum amount necessary to achieve desired pore volume in the crosslinked organo-amine materials of this disclosure. In general, depending on the size of the reaction mixture, concentrations of porogens in the range of from about 1.0 weight percent to about 75 weight percent, preferably from about 5 weight percent to about 50 weight percent, and more preferably from about 10 weight percent to about 30 weight percent, with respect to the overall reaction mixture, should be sufficient for most processes.

Reaction conditions for the reaction of the organo-halide starting material with the organo-amine starting material, such as temperature, pressure and contact time, may vary greatly. Any suitable combination of such conditions may be employed herein that are sufficient to produce the crosslinked organo-amine materials of this disclosure. Preferred reaction pressure is less than about 100 psig. More preferably, the reaction pressure is approximately ambient (atmospheric) pressure. Preferred reaction temperatures can range from about 0° C. to about 150° C., more preferably from about 25° C. to about 95° C. The preferred reaction time of the organo-halide with the organo-amine can range from about 60 seconds to about 48 hours. In an embodiment, the reaction is carried out under ambient pressure and the contact time may vary from a matter of seconds or minutes to a few hours or greater. The reactants can be added to the reaction mixture or combined in any order. The stir time employed is preferably from about 1 minute to about 48 hours, more preferably from about 1 hour to 24 hours, and even more preferably from about 2 hours to 8 hours. Isolation of the crosslinked organo-amine materials may be achieved by any techniques known in the art, such as solvent evaporation or nonsolvent extraction and other conventional procedures, to afford the final material.

The acid gas adsorption-desorption materials of this disclosure comprise in part linear organo-amine polymeric materials. Preferably, the linear organo-amine materials have a weight average molecular weight of from about 160 to about $1 \times 10^6$, preferably a weight average molecular weight of from about 400 to about $1 \times 10^5$, and more preferably a weight average molecular weight of from about 600 to about $1 \times 10^4$. Preferably, the linear organo-amine materials have an adsorption capacity of at least about 0.2 millimoles of $CO_2$ adsorbed per gram of adsorption-desorption material, preferably an adsorption capacity of at least about 0.5 millimoles of $CO_2$ adsorbed per gram of adsorption-desorption material, and more preferably an adsorption capacity of at least about 1.0 millimoles of $CO_2$ adsorbed per gram of adsorption-desorption material. This disclosure also includes mixtures of the linear organo-amine materials.

Illustrative linear organo-amine materials of this disclosure have a formula selected from:

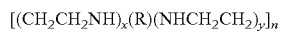

$$[(CH_2CH_2NH)_x(R)(NHCH_2CH_2)_y]_n$$

wherein x is an integer greater than about 1.0, y is an integer greater than about 1.0, n is an integer equal to or greater than about 1.0, the $CH_2CH_2NH$ and $NHCH_2CH_2$ groups can be linear or branched, and R is the same or different and is an alkyl or aryl moiety. In a preferred embodiment, at least one R is an aryl moiety. The structure can be terminated with either of the starting monomers as well as monofunctional amines and monofunctional aryl and/or alkyl halides.

The organo halide and organo-amine monomers can both or independently be difunctional and/or multifunctional. In cases where both monomers are difunctional, the product will be a linear organo-amine polymer. If either the organo halide or organo-amine monomers have at least three functional groups, the product will be a crosslinked organo-amine polymer.

The composition of the linear organo-amine materials of this disclosure, including all polymers, copolymers and terpolymers thereof, can vary over a wide range, and need only be that amount necessary to provide the desired adsorption-desorption properties. These materials can be formed as bulk solids, films, membranes and/or particulates.

Preferably, the linear organo-amine polymer materials of this disclosure have an average particle diameter of from about 0.1 microns to about 500 microns, preferably from about 1.0 microns to about 100 microns, and more preferably from about 2 microns to about 50 microns. Preferably, the linear organo-amine polymer materials of this disclosure have a total pore volume of from about 0.2 cubic centimeters per gram (cc/g) to about 2.0 cc/g, preferably from about 0.4 cc/g to about 2.0 cc/g, and more preferably from about 0.5 cc/g to about 2.0 cc/g, as measured by mercury porsimetry in cubic centimeters of pore volume per gram of the porous crosslinked organo-amine materials, for all pores having a diameter of 0.005 microns to 10 microns.

Preferably, the linear organo-amine polymer materials of this disclosure have an average pore size of from about 0.01 microns to about 1000 microns, preferably from about 0.1 microns to about 100 microns, and more preferably from about 1.0 microns to about 10 microns. Preferably, the linear organo-amine polymer materials of this disclosure have a surface area of from about 5 square meters per gram ($m^2/g$) to about 50 $m^2/g$, preferably from about 20 $m^2/g$ to about 50 $m^2/g$, and more preferably from about 25 $m^2/g$ to about 50 $m^2/g$, as measured by mercury porsimetry.

The linear organo-amine materials of this disclosure can be prepared by a process that involves reacting at least one organo halide material with at least one organo-amine material under conditions sufficient to produce the linear organo-amine material. In particular, the linear organo-amine materials can be produced by reacting at least one organo halide or mixtures of organo halides, with at least one linear amine, or mixtures thereof, under conditions sufficient to produce the linear organo-amine material.

Illustrative organo halide starting materials useful in making the linear organo-amine materials of this disclosure may be selected from a wide variety of materials known in the art. Illustrative organo halide starting materials include, for example, benzylic halide and mixtures thereof. Preferably, the organo halide is selected from methylbenzyl chloride, dichloro-p-xylene, crosslinked polystyrene spheres with chemically attached chloromethylstyrene, and mixtures thereof. The organo halide materials can be prepared by conventional methods known in the art and/or are commercially available.

Illustrative organo-amine starting materials useful in making the linear organo-amine materials of this disclosure may be selected from a wide variety of materials known in the art. Illustrative organo-amine starting materials include, for example, primary amines, secondary amines, and mixtures thereof. Suitable polyamines include, for example, linear polyamines, linear polyalkyleneimines, and mixtures thereof. Preferably, the organo-amine is selected from propylenediamine, tetraethylenepentaamine, linear polyethyleneimines, and mixtures thereof. The organo-amine materials can be prepared by conventional methods known in the art and/or are commercially available As indicated above, mixtures of organo halide starting materials can be used in making the linear organo-amine materials of this disclosure. For example, one or more aromatic compounds having at least two haloalkyl functional groups may be used in the halide starting material mixtures in the process of this disclosure. These compounds may be used alone or in combination with the alkyl halide compounds described below. Illustrative aromatic compounds having at least two haloalkyl functional groups include, for example, 2,4-bis(chloromethyl)-1,3,5-trimethylbenzene, 2,4,6-tris-(chloromethyl)-mesitylene, 1,3,5-tris-chloromethyl-2,4,6-trimethylbenzene, and mixtures thereof. These aromatic compounds having at least two haloalkyl functional groups can be prepared by conventional methods known in the art and/or are commercially available.

One or more alkyl halides may also be used as starting materials in the process of this disclosure. These compounds may be used alone or in combination with the aromatic (or "arene" or "aryl") compounds having at least two haloalkyl functional groups described above. Illustrative alkyl halides include, for example, polyhalo-alkanes and polyhalo-alkenes having from 1 to about 12 carbon atoms. The polyhalo-alkanes and polyhalo-alkenes can be linear or branched, and contain two or more halide groups with no limit placed on their location on the alkane or alkene chain. The alkene chain can contain one or more carbon-carbon multiple bonds of indeterminate location on the chain. Mixtures of alkyl halides are also useful in this disclosure. These alkyl halide starting materials can be prepared by conventional methods known in the art and/or are commercially available.

One or more porogens may also be used as a component material in the fabrication processes and linear polymers of this disclosure. An interpenetrating network of holes, closed cells or a combination thereof can be achieved in the linear polymers of this disclosure by polymerization in the presence of an insoluble material such as a porogen. Subsequent removal of the porogen gives rise to interstices throughout the formed linear polymer material. Porogen concentrations in the range of from about 1.0 weight percent to about 75 weight percent, preferably from about 5 weight percent to about 50 weight percent, and more preferably from about 10 weight percent to about 30 weight percent, with respect to the overall reaction mixture, should be sufficient for most processes.

Illustrative porogens include, for example, xylene, toluene, polyvinylpyrrolidinone, and mixtures thereof. The porogens can be prepared by conventional methods known in the art and/or are commercially available.

The concentration of the organo halide starting material in the process of this disclosure can vary over a wide range, and need only be that minimum amount necessary to react with the amine starting material and to provide the linear organo-amine materials of this disclosure. In general, depending on the size of the reaction mixture, organo halide starting material concentrations in the range of from about 1.0 weight percent to about 75 weight percent, preferably from about 5 weight percent to about 50 weight percent, and more preferably from about 10 weight percent to about 30 weight percent, with respect to the overall reaction mixture, should be sufficient for most processes.

The concentration of the organo-amine starting material in the process of this disclosure can vary over a wide range, and need only be that minimum amount necessary to react with the organo halide starting material and to provide the linear organo-amine materials of this disclosure. In general, depending on the size of the reaction mixture, organo-amine starting material concentrations in the range of from about 1.0 weight percent to about 75 weight percent, preferably from about 5 weight percent to about 50 weight percent, and more preferably from about 10 weight percent to about 30 weight percent, with respect to the overall reaction mixture, should be sufficient for most processes.

The concentration of the porogens in the process of this disclosure can vary over a wide range, and need only be that minimum amount necessary to achieve desired pore volume in the linear organo-amine materials of this disclosure. In general, depending on the size of the reaction mixture, concentrations of porogens in the range of from about 1.0 weight percent to about 75 weight percent, preferably from about 5 weight percent to about 50 weight percent, and more preferably from about 10 weight percent to about 30 weight percent, with respect to the overall reaction mixture, should be sufficient for most processes.

Reaction conditions for the reaction of the organo halide starting material with the amine starting material, such as temperature, pressure and contact time, may vary greatly. Any suitable combination of such conditions may be employed herein that are sufficient to produce the linear organo-amine materials of this disclosure. Preferred reaction pressure is less than about 100 psig. More preferably, the reaction pressure is approximately ambient (atmospheric) pressure. Preferred reaction temperatures can range from about 0° C. to about 150° C., more preferably from about 25° C. to about 95° C. The preferred reaction time of the organo halide with the organo-amine can range from about 60 seconds to about 48 hours. In an embodiment, the reaction is carried out under ambient pressure and the contact time may vary from a matter of seconds or minutes to a few hours or greater. The reactants can be added to the reaction mixture or combined in any order. The stir time employed is preferably from about 1 minute to about 48 hours, more preferably from about 1 hour to 24 hours, and even more preferably from about 2 hours to 8 hours. Isolation of the linear organo-amine materials may be achieved by any techniques known in the art, such as solvent evaporation, nonsolvent extraction and other conventional methods, to afford the final material.

The method of this disclosure involves removing $CO_2$ and/or other acid gases, such as $H_2S$, from a gaseous stream containing one or more of these gases. The method of this disclosure is based on the selective adsorption of a gas mixture and involves contacting the gas mixture with a selective adsorbent in an adsorption zone. The adsorption zone is maintained at adsorption conditions (i.e., temperature and/or pressure) favorable to selectively adsorbing a component of the gas mixture and producing an adsorption effluent, which has reduced concentration of the adsorbed component relative to the gas mixture. Subsequently, the adsorbed component is then desorbed by changing the conditions in the adsorption zone to induce desorption. Alternatively, the selective adsorbent can be moved from the adsorption zone to a desorption zone having conditions favorable for desorption. Under desorption conditions, at least a portion of the adsorbed component is desorbed from the selective adsorbent. Following the desorptive step, the adsorption zone may be further purged with a purge gas to further remove the adsorbed component.

Once the adsorbent has been synthesized, it can be employed in a sorbent bed for use the adsorption-desorption process. Preferably, the adsorbent of this disclosure should be formed into a stable, mechanically strong form. These forms may include, for example, pellet forms or monolithic structures. The selection of the appropriate form is based on the application of the adsorbent and the type of equipment used. After the adsorbent form is selected and manufactured, it is used in a sorbent bed where a gaseous stream containing $CO_2$ contacts the adsorbent. In the adsorption process, the $CO_2$ and amine chemically react to form an amine complex, thereby removing the $CO_2$ from the gaseous stream.

After the adsorbent is loaded with $CO_2$ to a satisfactory level, for example, when greater than 80 percent of the amine has been converted to the amine complex, or at a designated cycle time, the adsorbent can be regenerated. Regeneration involves ceasing the flow of the gaseous stream through the bed and desorbing the adsorbed $CO_2$. The desorption can be accomplished by controlled temperature swing, pressure swing, partial pressure swing, or by the use of a sweeping or purge gas, or any combination thereof. During this step, the amine complex is dissociated, and $CO_2$ removed and the amine is freed and ready for re-use. In an embodiment, the adsorption-desorption can be carried out under essentially isothermal conditions.

The adsorbent material of this disclosure comprises a crosslinked organo-amine material or a linear organo-amine material. Suitable crosslinked organo-amine materials and linear organo-amine materials of this disclosure are described more fully herein.

The adsorbent material has an adsorption capacity of at least about 0.2 millimoles, preferably at least about 0.5 millimoles, and more preferably at least about 1.0 millimoles, of $CO_2$ adsorbed per gram of adsorbent when measured by a thermal gravimetric apparatus using a dry gas stream containing $CO_2$ (about 0.7 atmosphere partial pressure) and an inert gas. The adsorbent can be regenerated from one cycle to another in cycling adsorption processes, and thus the adsorbent is cyclically stable.

The adsorption beds can be configured in a variety of ways, for example, moving beds and fixed beds. The configuration is preferably fixed bed wherein the fixed bed is fixed relative to the flow of the feedstream through the bed. In a moving bed configuration, the adsorbent in the adsorption bed and the gas mixture move through the adsorption zone in a continuous manner. Then the adsorbent is moved from the adsorption zone into the desorption zone.

In the preferred fixed bed configuration, the bed is fixed in a certain area of the cyclic adsorption apparatus and contains the adsorbent. The gas mixture passes through the fixed bed while under adsorption zone conditions. After a period of time when the adsorbent adsorbs a portion of the gas mixture, the conditions are changed in the area that includes the fixed bed to desorption zone conditions to desorb the adsorbed gases. Many cyclic adsorption apparatus configurations can include two or more fixed beds in separate regions or the apparatus, so that while one fixed bed is under adsorption conditions, the other fixed bed is under desorption conditions. Therefore, the gas stream can be operated in a continuous manner.

In general, for temperature swing adsorption processes, the temperature in the adsorption zone is lower than the temperature in the desorption zone, while the pressure is substantially constant. For pressure swing adsorption processes, the pressure in the adsorption zone is greater than the pressure of the desorption zone, while the temperature is substantially constant.

The temperature of the adsorption zone for cyclic adsorption processes depends upon a number of factors, such as the particular hydrocarbons present in the gas mixture being separated, the particular adsorbent being used, and the pressure at which the adsorption step is carried out. The upper and lower temperatures at which the adsorption zone is maintained is, in part, determined by both economics and the chemical reactivity of the components in the gas mixture. In particular, the temperature at which the adsorption zone is maintained should be below the temperature at which the gas mixture components undergo chemical reaction (e.g., hydrocarbons undergoing oligomerization and polymerization).

For the adsorption processes of this disclosure, the temperature of the inlet stream is preferably in the range of from about 20° C. to about 150° C., more preferably from about 75° C. to about 125° C., and even more preferably greater than about 80° C. In a preferred embodiment, the adsorption-desorption is carried out under essentially isothermal conditions. The pressure during adsorption is preferably in the range of from about 0.1 bar to about 300 bar (absolute), more preferably from about 0.1 bar to about 150 bar (absolute). The partial pressure of carbon dioxide in the gas mixture is preferably from about 0.1 to about 150 bar, more preferably from about 0.1 to about 20 bar, and even more preferably from about 0.1 to about 10 bar (absolute). The gas mixture can be contacted with the adsorbent bed material at a gas hourly space velocity (GHSV) of from about 200 to about 50,000 GHSV. The gas mixture can be contacted with the adsorbent material in the processes of this disclosure one or more times.

The carbon dioxide can be desorbed from the adsorbent material by any conventional methods. One possibility is to desorb the carbon dioxide by means of a helium purge. Other possibilities include pressure swing adsorption including partial pressure swing adsorption, thermal swing adsorption, rapid cycle partial pressure swing to adsorption, or any combination thereof.

For desorption, suitable pressures can range from preferably about 50 millibar to about 75 bar (absolute), more preferably from about 50 millibar to about 3 bar (absolute), even more preferably from about 100 millibar to about 1.5 bar (absolute). The temperature is preferably in the range of from about 50° C. to about 150° C., more preferably from about 75° C. to about 125° C., and even more preferably greater than about 80° C. In a preferred embodiment, the adsorption-desorption is carried out under essentially isothermal conditions.

For temperature swing adsorption processes, adsorbent regeneration is carried out at a temperature higher than the adsorption temperature and below the temperature at which undesired reactions of the components of the gas mixture take place. For temperature swing adsorption processes, the adsorbent regeneration temperature is typically in the range of about 40° C. to less than about 200° C., preferably from about 60° C. to about 140° C. The pressures at which the adsorption and adsorbent regeneration steps are carried out are not critical for temperature swing adsorption processes, and in general these steps can be carried out at any of the usual pressures employed for cyclic adsorption processes.

It is understood that the adsorbent is not limited to use for the removal of $CO_2$ from a gaseous stream. Rather the adsorbent can be used for the removal of any acid gas, or combination thereof, from a gaseous stream, provided that the acid gas is capable of reaction with amines.

The gas mixture containing carbon dioxide can originate from a natural or artificial source. The gas mixture can contain in addition to carbon dioxide, one or more other gases such as methane, ethane, n-butane, i-butane, hydrogen, carbon monoxide, ethene, ethyne, propene, nitrogen, oxygen, helium, neon, argon, krypton, and hydrogen sulfide.

The constituents of the gas mixture may have different proportions. The amount of carbon dioxide in the gas mixture is preferably at least 1 percent by volume, more preferably at least 10 percent by volume, and even more preferably 50 percent by volume or greater. The gas mixture can be any of a variety of gases, for example, natural gas, flue gas, fuel gas, waste gas and air.

The contacting of the gas mixture can be carried out by continuous adsorption on a fixed bed. The gas mixture is passed through the fixed adsorbent bed. Continuous adsorption can take place in two or more adsorbent beds in which at least one of the adsorbent beds contains the crosslinked organo-amine material or linear organo-amine material or a combination thereof.

The gas mixture can be subject to dehumidification prior to contacting with the adsorbent material. The dehumidification can be carried out by conventional methods. For example, the dehumidification can be carried out by adsorption over fixed bed reactors containing solid sorbents. Preferred solid sorbents include, for example, molecular sieves, silica gels or aluminas.

It will be appreciated that conventional equipment can be used to perform the various functions of the cyclic processes, such as monitoring and automatically regulating the flow of gases within the cyclic adsorption system so that it can be fully automated to run continuously in an efficient manner.

Various modifications and variations of this disclosure will be obvious to a worker skilled in the art and it is to be understood that such modifications and variations are to be included within the purview of this application and the spirit and scope of the claims.

Example 1

The reaction of $\alpha,\alpha'$-dichloro-p-xylene (DCX) with tetraethylenepentaamine (TEPA) produces an essentially linear polymeric structure, while the reaction of DCX with a polyethyleneimine produces a chemically crosslinked structure. The level of crosslinking is directly related to the initial stoichiometry ratio of DCX, TEPA and the polyethyleneimine, and mixtures thereof, as well as the reaction temperature. At high levels of TEPA addition, the product will contain both chemical crosslinks and pendant (i.e., branched) TEPA moieties. At high levels of polyethyleneimine addition, the product will contain both chemical crosslinks and pendant (i.e., branched) polyethyleneimine moieties.

The reaction of benzylic halides with primary amines produces secondary amines, and the reaction of benzylic halides with secondary amines produces tertiary amines. Low temperatures can be used to facilitate the formation of secondary amines. High temperatures can be used to facilitate the formation of linear and branched structures, i.e., the formation of secondary and tertiary amines.

Example 2

0.75 grams of DCX was dissolved in dry 48.5 milliliters of toluene while purging with nitrogen gas. Agitation was provided with a mechanical stirrer. Subsequently, 3.62 grams of a polyethyleneimine (number average molecular weight 423) was added dropwise into the toluene solution. At all times, the synthesis was performed at room temperature. Initially, the solution was optically clear. However, as the reaction proceeded, the solution began to turn cloudy. Within a few hours an "oil-like" material appeared in the flask. After several days had elapsed, the solvent was evaporated by application of a vacuum. 50 milliliters of acetone was added with continual stirring for 30 minutes. The resultant solid material was separated by centrifugation. Finally, a 2% solution of NaOH/methanol (50 milliliters) was added with continual stirring. The white precipitate was collected, washed with deionized water and dried. This material was used in the subsequent absorption measurements presented in the following examples.

Example 3

1.5 grams of DCX (8.58 mmoles) was dissolved in toluene (48.5 milliliters). Subsequently, 1.62 grams of TEPA (8.58 mmoles) was added to the solution in a dropwise fashion. After about 20 minutes, the initially clear solution began to turn cloudy. The solution was agitated at room temperature for approximately 12 hours. The solid material was isolated, neutralized and dried as in the previous examples. NMR analysis is consistent with the anticipated structure for a difunctional monomer capable of being chemically crosslinked.

Example 4

$CO_2$ absorption data as a function of temperature and pressure is shown in FIG. 1 for the adsorbent of Example 2. The graph shows that this adsorbent material is highly effective in absorbing carbon dioxide from the feed stream. The desorption process is also effective at higher temperatures.

Example 5

Figure 2:
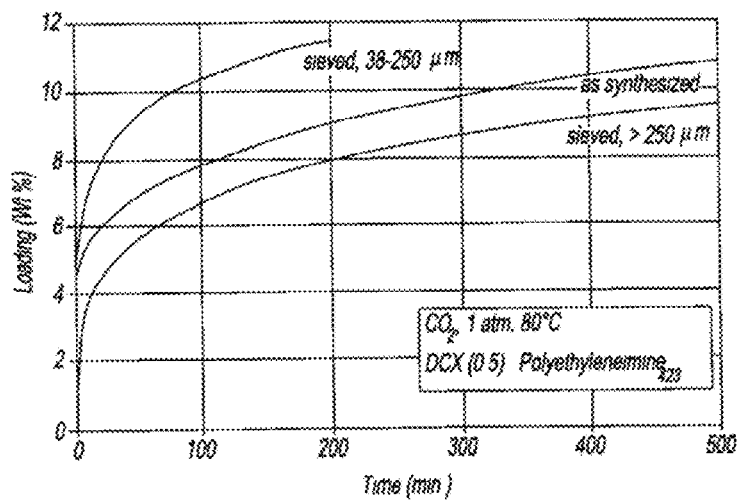
FIG. 2 graphically depicts diffusion time as a function of particle size for the adsorbent used in Example 2.

Diffusion time as a function of particle size is show in FIG. 2 for the adsorbent of Example 2. Decreased particle size provides higher surface area for absorption to occur. Absorption kinetics were also enhanced.

Example 6

FIG. 3 shows data from a variety of polyethyleneimine and aminosilane-modified materials. With the exception of an aqueous solution of pure polyethyleneimine, the adsorbent material of this disclosure (i.e., DCX-Polyethyleneimine 423) exhibits superior $CO_2$ uptake capacity than all of the comparative materials tested at a substantially higher temperature. Note that the closest capacity material (GT-HAS) suffers considerable capacity loss at an adsorption temperature of 75° C. The data for AP-SBA, Diamine-SBA, Polyethyleneimine-SBA, TEPA-SBA and GT-HAS was collected in humidified $CO_2$. The sorbents listed in FIG. 3 are identified as follows: Polyethyleneimine 423/$SiO_2$=polyethyleneimine with average molecular weight of 423 impregnated into amorphous silica; AP-SBA=aminopropylsilane modified mesoporous silica; Diamine-SBA=2-aminoethyl-aminopropylsilane modified mesoporous silica; Polyethyleneimine 423/SBA (olig.) =polyethyleneimine with average molecular weight of 423 impregnated into mesoporous silica; Polyethyleneimine/ SBA (750K)=polyethyleneimine with average molecular weight of 750,000 impregnated into mesoporous silica; TEPA-SBA=tetraethylenepentamine impregnated mesoporous silica; GT-HAS=hyperbranched aminosilica material available from Georgia Tech, Atlanta, Ga.; DCX (dichloroxylene)-Polyethyleneimine 423=copolymer of dichloroxylene-polyethyleneimine prepared according to Example 2; and Pure Polyethyleneimine=15 percent aqueous solution (molecular weight of 433).

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

What is claimed is:

1. An acid gas adsorption-desorption material comprising a linear organo-amine material having a weight average molecular weight of from about 160 to about $1\times10^6$, a total pore volume of from about 0.2 cubic centimeters per gram (cc/g) to about 2.0 cc/g, and an adsorption capacity of at least about 0.2 millimoles of $CO_2$ adsorbed per gram of adsorption-desorption material, or mixtures thereof; wherein said linear organo-amine material is produced by reacting at least one organo halide comprised of at least two haloalkyl functional groups, with at least one organo-amine, said at least one organo-amine comprising a linear amine, under conditions sufficient to produce said linear organo-amine material.

2. The acid gas adsorption-desorption material of claim 1 wherein said at least one organo halide is comprised of an aromatic organo halide.

3. The acid gas adsorption-desorption material of claim 2 wherein said aromatic organo halide is selected from the group consisting of: methylbenzyl chloride, dichloro-p-xylene, crosslinked polystyrene spheres with chemically attached chloromethylstyrene, and mixtures thereof, and said at least one organo-amine is selected from the group consisting of: propylenediamine, tetraethylenepentaamine, polyethyleneimines, and mixtures thereof.

4. The acid gas adsorption-desorption material of claim 2 wherein said aromatic organo halide is selected from the group consisting of: 2,4-bis(chloromethyl)-1,3,5-trimethylbenzene, 2,4,6-tris-(chloromethyl)-mesitylene, 1,3,5-tris-chloromethyl-2,4,6-trimethylbenzene, and mixtures thereof.

5. The acid gas adsorption-desorption material of claim 1 wherein said at least one organo halide is comprised of an alkyl organo halide.

6. The acid gas adsorption-desorption material of claim 5 wherein said alkyl organo halide is selected from the group consisting of polyhalo-alkanes and polyhalo-alkenes having from 1 to 12 carbon atoms, and mixtures thereof.

7. The acid gas adsorption-desorption material of claim 1 wherein said at least one organo-amine comprises a primary amine, a secondary amine, or mixtures thereof, and said at least one organo-amine is a polyamine that comprises a linear polyamine.

8. The acid gas adsorption-desorption material of claim 1 wherein said linear organo-amine material has a formula selected from:

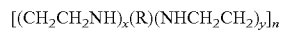
$[(CH_2CH_2NH)_x(R)(NHCH_2CH_2)_y]_n$ wherein x is an integer greater than about 1.0, y is an integer greater than about 1.0, n is an integer equal to or greater than about 1.0, the $CH_2CH_2NH$ and $NHCH_2CH_2$ groups can be linear or branched, and R is the same or different and is an alkyl or aryl moiety.

9. The acid gas adsorption-desorption material of claim 8 wherein R is comprised of at least one aryl moiety.

10. The acid gas adsorption-desorption material of claim 1 wherein said linear organo-amine material has an average particle diameter of from about 0.1 microns to about 500 microns.

* * * * *